United States Patent
Delzer

(10) Patent No.: US 6,646,187 B2
(45) Date of Patent: Nov. 11, 2003

(54) INBRED MAIZE LINE NP2073

(75) Inventor: Brent Delzer, Janesville, WI (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/770,701

(22) Filed: Jan. 26, 2001

(65) Prior Publication Data

US 2002/0144311 A1 Oct. 3, 2002

(51) Int. Cl.$^7$ .............................. C12N 5/04; A01H 5/00; A01H 5/10; A01H 1/00; A01H 1/02
(52) U.S. Cl. .................... 800/320.1; 800/260; 800/268; 800/275; 800/266; 800/265; 800/271; 800/274; 800/288; 800/300.1; 800/302; 800/303; 435/412; 435/419; 435/421; 435/424; 435/430; 435/430.1; 435/468
(58) Field of Search .................. 435/412, 419, 435/421, 424, 430, 430.1, 468; 800/260, 265, 275, 266, 267, 268, 278, 271, 274, 320.1, 288, 300.1, 303, 302, 301

(56) References Cited

U.S. PATENT DOCUMENTS 5,523,520 A * 6/1996 Hunsperger et al. ........ 800/200
5,792,906 A * 8/1998 Mies .......................... 800/200
6,184,444 B1   2/2001 Delzer ..................... 800/320.1

OTHER PUBLICATIONS

Eshed et al, "Less–Than–Additive Epistatic Interactions of Quantitative Trait Loci in Tomato", 1996, Genetics vol. 143, pp. 1807–1817.*

Kraft et al, "Linkage disequilibrium and fingerprinting in sugar beet", 2000, Theor Appl Genet, vol. 101. pp. 323–326.*

Allard, Robert, Principles of Plant Breeding, 2nd edition, pp. 188–197, 1999.*

AgBiosafety. Overview of the Process of Process of Plant Genetic Engineering. University of Nebraska, 2001.*

* cited by examiner

Primary Examiner—David T. Fox
Assistant Examiner—Medina A. Ibrahim
(74) Attorney, Agent, or Firm—Bruce Vrana

(57) ABSTRACT

An inbred maize line, designated NP2073, the plants and seeds of inbred maize line NP2073 and descendants thereof, methods for producing a maize plant produced by crossing the inbred line NP2073 with itself or with another maize plant, and hybrid maize seeds and plants produced by crossing the inbred line NP2073 with another maize line or plant

17 Claims, No Drawings

INBRED MAIZE LINE NP2073

FIELD OF THE INVENTION

This invention is in the field of maize breeding, specifically relating to an inbred maize line designated NP2073.

BACKGROUND OF THE INVENTION

The goal of plant breeding is to combine in a single variety or hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant. Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Maize (*Zea mays* L.), often referred to as corn in the United States, can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears.

A reliable method of controlling male fertility in plants offers the opportunity for improved plant breeding. This is especially true for development of maize hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid maize seed is typically produced by a male sterility system incorporating manual or mechanical detasseling. Alternate strips of two maize inbreds are planted in a field, and the pollen-bearing tassels are removed from one of the inbreds (female). Providing that there is sufficient isolation from sources of foreign maize pollen, the ears of the detasseled inbred will be fertilized only from the other inbred (male) and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Seed from detasseled fertile maize and CMS produced seed of the same hybrid can be blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 and chromosomal translocations as described in U.S. Pat. Nos. 3,861,709 and 3,710,511, the disclosures of which are specifically incorporated herein by reference. There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: publications EPO 89/3010153.8 and WO 90/08828).

Another system useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904, which is incorporated herein by reference). Application of the gametocide, timing of the application and genotype specificity often limit the usefulness of the approach.

The use of male sterile inbreds is but one factor in the production of maize hybrids. The development of maize hybrids requires, in general, the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1 to F2; F3 to F4; F4 to F5; etc.

A single cross maize hybrid results from the cross of two inbred lines, each of which has a genotype that complements the genotype of the other. The hybrid progeny of the first generation is designated F1. In the development of commercial hybrids only the F1 hybrid plants are sought. Preferred F1 hybrids are more vigorous than their inbred parents. This hybrid vigor, or heterosis, can be manifested in many polygenic traits, including increased vegetative growth and increased yield.

The development of a maize hybrid involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny (F1). During the inbreeding process in maize, the vigor of the lines decreases. Vigor is restored when two different inbred lines are crossed to produce the hybrid progeny (F1). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the F1 progeny. A double cross hybrid is produced from four inbred lines crossed in pairs (A×B and C×D) and then the two F1 hybrids are crossed again (A×B)× (C×D). Much of the hybrid vigor exhibited by F1 hybrids is lost in the next generation (F2). Consequently, seed from hybrids is not used for planting stock.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed. Once the seed is planted, it is possible to identify and select these self-pollinated plants. These self-pollinated plants will be genetically equivalent to the female inbred line used to produce the hybrid. Typically these self-pollinated plants can be identified and selected due to their decreased vigor. Female selfs are identified by their less vigorous appearance for vegetative and/or reproductive characteristics, including shorter plant height, small ear size, ear and kernel shape, cob color, or other characteristics.

Identification of these self-pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pp. 1–8 (1995), the disclosure of which is expressly incorporated herein by reference. Through these technologies, the homozygosity of the self-pollinated line can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritca si Aplicata Vol. 20 (1) p. 29–42.

As is readily apparent to one skilled in the art, the foregoing are only two of the various ways by which the inbred can be obtained by those looking to use the germplasm. Other means are available, and the above examples are illustrative only.

Maize is an important and valuable field crop. Thus, a continuing goal of plant breeders is to develop high-yielding maize hybrids that are agronomically sound based on stable inbred lines. The reasons for this goal are obvious: to maximize the amount of grain produced with the inputs used and minimize susceptibility of the crop to pests and environmental stresses. To accomplish this goal, the maize breeder must select and develop superior inbred parental lines for producing hybrids. This requires identification and selection of genetically unique individuals that occur in a segregating population. The segregating population is the result of a combination of crossover events plus the independent assortment of specific combinations of alleles at many gene loci that results in specific genotypes. The probability of selecting any one individual with a specific genotype from a breeding cross is infinitesimal due to the large number of segregating genes and the unlimited recombinations of these genes, some of which may be closely linked. However, the genetic variation among individual progeny of a breeding cross allows for the identification of rare and valuable new genotypes. These new genotypes are neither predictable nor incremental in value, but rather the result of manifested genetic variation combined with selection methods, environments and the actions of the breeder. Thus, even if the entire genotypes of the parents of the breeding cross were characterized and a desired genotype known, only a few, if any, individuals having the desired genotype may be found in a large segregating F2 population. Typically, however, neither the genotypes of the breeding cross parents nor the desired genotype to be selected is known in any detail. In addition, it is not known how the desired genotype would react with the environment. This genotype by environment interaction is an important, yet unpredictable, factor in plant breeding. A breeder of ordinary skill in the art cannot predict the genotype, how that genotype will interact with various climatic conditions or the resulting phenotypes of the developing lines, except perhaps in a very broad and general fashion. A breeder of ordinary skill in the art would also be unable to recreate the same line twice from the very same original parents, as the breeder is unable to direct how the genomes combine or how they will interact with the environmental conditions. This unpredictability results in the expenditure of large amounts of research resources in the development of a superior new maize inbred line.

SUMMARY OF THE INVENTION

According to the invention, there is provided a novel inbred maize line, designated NP2073. This invention thus relates to the seeds of inbred maize line NP2073, to the plants of inbred maize line NP2073, and to methods for producing a maize plant by crossing the inbred line NP2073 with itself or another maize line. This invention further relates to hybrid maize seeds and plants produced by crossing the inbred line NP2073 with another maize line.

The invention is also directed to inbred maize line NP2073 into which one or more specific, single gene traits, for example transgenes, have been introgressed from another maize line. Preferably, the resulting line has essentially all of the morphological and physiological characteristics of inbred maize line of NP2073, in addition to the one or more specific, single gene traits introgressed into the inbred, preferably the resulting line has all of the morphological and physiological characteristics of inbred maize line of NP2073, in addition to the one or more specific, single gene traits introgressed into the inbred. The invention also relates to seeds of an inbred maize line NP2073 into which one or more specific, single gene traits have been introgressed and to plants of an inbred maize line NP2073 into which one or more specific, single gene traits have been introgressed. The invention further relates to methods for producing a maize plant by crossing plants of an inbred maize line NP2073 into which one or more specific, single gene traits have been introgressed with themselves or with another maize line. The invention also further relates to hybrid maize seeds and plants produced by crossing plants of an inbred maize line NP2073 into which one or more specific, single gene traits have been introgressed with another maize line. The invention is also directed to a method of producing inbreds comprising planting a collection of hybrid seed, growing plants from the collection, identifying inbreds among the hybrid plants, selecting the inbred plants and controlling their pollination to preserve their homozygosity.

DEFINITIONS

In the description and examples that follow, a number of terms are used herein. In order to provide a clear and consistent understanding of the specification and claims, including the scope to be given such terms, the following definitions are provided. Below are the descriptors used in the data tables included herein. All linear measurements are in centimeters unless otherwise noted.

| | |
|---|---|
| Heat units | (Max Temp(<=86 deg. F.) + Min Temp(>=50 deg. F.))/2 − 50 |
| EMRGN | Final number of plants per plot |
| KRTP | Kernel type: 1. sweet 2. dent 3. flint 4. flour 5. pop 6. ornamental 7. pipecorn 8. other |
| ERTLP | % Root lodging (before anthesis) |
| GRNSP | % Brittle snapping (before anthesis) |
| TBANN | Tassel branch angle of 2nd primary lateral branch (at anthesis) |
| LSPUR | Leaf sheath pubescence of second leaf above the ear (at anthesis) 1–9 (1 = none) |
| ANGBN | Angle between stalk and 2nd leaf above the ear (at anthesis) |
| CR2L | Color of 2nd leaf above the ear (at anthesis) |
| GLCR | Glume Color |
| GLCB | Glume color bars perpendicular to their veins (glume bands): 1. absent 2. present |
| ANTC | Anther color |
| PLQUR | Pollen Shed: 0–9 (0 = male sterile) |
| HU1PN | Heat units to 10% pollen shed |
| HUPSN | Heat units to 50% pollen shed |
| SLKC | Silk color |
| HU5SN | Heat units to 50% silk |
| SLK5N | Days to 50% silk in adapted zone |
| HU9PN | Heat units to 90% pollen shed |
| HUPLN | Heat units from 10% to 90% pollen shed |
| DA19 | Days from 10% to 90% pollen shed |
| LAERN | Number of leaves above the top ear node |
| MLWVR | Leaf marginal waves: 1–9 (1 = none) |
| LFLCR | Leaf longitudinal creases: 1–9 (1 = none) |
| ERLLN | Length of ear leaf at the top ear node |
| ERLWN | Width of ear leaf at the top ear node at the widest point |
| PLHCN | Plant height to tassel tip |
| ERHCN | Plant height to the top ear node |
| LTEIN | Length of the internode between the ear node and the node above |
| LTASN | Length of the tassel from top leaf collar to tassel tip |
| LTBRN | Number of lateral tassel branches that originate from the central spike |
| EARPN | Number of ears per stalk |
| APBRR | Anthocyanin pigment of brace roots: 1. absent 2. faint 3. moderate 4. dark |
| TILLN | Number of tillers per plant |
| HSKC | Husk color 25 days after 50% silk (fresh) |
| HSKD | Husk color 65 days after 50% silk (dry) |
| HSKTR | Husk tightness 65 days after 50% silk: 1–9 (1 = loose) |
| HSKCR | Husk extension: 1. short (ear exposed) 2. medium (8 cm) 3. long (8–10 cm) 4. very long (>10 cm) |
| HEPSR | Position of ear 65 days after 50% silk: 1. upright 2. horizontal 3. pendent |
| STGRP | % Staygreen at maturity |
| DPOPN | % dropped ears 65 days after anthesis |
| LRTRN | % root lodging 65 days after anthesis |
| HU25 | Heat units to 25% grain moisture |
| HUSG | Heat units from 50% silk to 25% grain moisture in adapted zone |
| DSGM | Days from 50% silk to 25% grain moisture in adapted zone |
| SHLNN | Shank length |
| ERLNN | Ear length |
| ERDIN | Diameter of the ear at the midpoint |
| EWGTN | Weight of a husked ear (grams) |
| KRRWR | Kernel rows: 1. indistinct 2. distinct |

-continued

| | |
|---|---|
| KRNAR | Kernel row alignment: 1. straight 2. slightly curved 3. curved |
| ETAPR | Ear taper: 1. slight 2. average 3. extreme |
| KRRWN | Number of kernel rows |
| COBC | Cob color |
| COBDN | Diameter of the cob at the midpoint |
| KRTP | Endosperm type: 1. sweet 2. extra sweet 3. normal 4. high amylose 5. waxy 6. high protein 7. high lysine 8. super sweet 9. high oil 10. other |
| KRCL | Hard endosperm color |
| ALEC | Aleurone color |
| ALCP | Aleurone color pattern: 1. homozygous 2. segregating |
| KRLNN | Kernel length (mm) |
| KRWDN | Kernel width (mm) |
| KRDPN | Kernel thickness (mm) |
| K100N | 100 kernel weight (grams) |
| KRPRN | % round kernels on 13/64 slotted screen |
| GRLSR | Grey leaf spot severity rating; 1 = resistent, 9 = susceptible. |
| INTLR | Intactness rating of plants at time of harvest; 1 = all foliage intact, 9 = all plants broken below the ear. |
| LRTLP | Percentage of plants lodged, leaning >30 degrees from vertical, but unbroken at harvest. |
| MST_P | Percent grain moisture at harvest. |
| SCLBR | Southern corn leaf blight severity rating; 1 = resistent, 9 = susceptible. |
| STKLP | Percentage of plants with stalks broken below the ear at time of harvest. |
| YBUAN | Grain yield expressed as bushels per acre adjusted to 15.5% grain moisture. |
| STBWR | Stewart Bacterial Wilt |
| ERLNN | Ear Length |
| CRSTR | Common Rust Rating |
| GRQUR | Grain Quality |
| PLTAR | Plant Appearance |
| HUBLN | Heat Units to Black Layer |
| TSTWN | Test Weight in LBS/BU |
| PSTSP | Push Test for Stalk/Root Quality on Erect Plants |
| ERGRR | Early Growth: 6+ Leaf Stage |

DETAILED DESCRIPTION OF THE INVENTION

Inbred maize lines are typically developed for use in the production of hybrid maize lines. Inbred maize lines need to be highly homogeneous, homozygous and reproducible to be useful as parents of commercial hybrids. There are many analytical methods available to determine the homozygotic and phenotypic stability of these inbred lines.

The oldest and most traditional method of analysis is the observation of phenotypic traits. The data is usually collected in field experiments over the life of the maize plants to be examined. Phenotypic characteristics most often observed are for traits associated with plant morphology, ear and kernel morphology, insect and disease resistance, maturity, and yield.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

Some of the most widely used of these laboratory techniques are Isozyme Electrophoresis and RFLPs as discussed in Lee, M., "Inbred Lines of Maize and Their Molecular Markers," The Maize Handbook, (Springer-Verlag, New York, Inc. 1994, at 423–432). Isozyme Electrophoresis is a useful tool in determining genetic composition, although it has relatively low number of available markers and the low number of allelic variants among maize inbreds. RFLPs have the advantage of revealing an exceptionally high degree of allelic variation in maize and the number of available markers is almost limitless. Maize RFLP linkage maps have been rapidly constructed and widely implemented in genetic studies. One such study is described in Boppenmaier, et al., "Comparisons among strains of inbreds for RFLPS", Maize Genetics Cooperative Newsletter, 65:1991, pg. 90. This study used 101 RFLP markers to analyze the patterns of 2 to 3 different deposits each of five different inbred lines. The inbred lines had been selfed from 9 to 12 times before being adopted into 2 to 3 different breeding programs. It was results from these 2 to 3 different breeding programs that supplied the different deposits for analysis. These five lines were maintained in the separate breeding programs by selfing or sibbing and rogueing off-type plants for an additional one to eight generations. After the RFLP analysis was completed, it was determined the five lines showed 0–2% residual heterozygosity. Although this was a relatively small study, it can be seen using RFLPs that the lines had been highly homozygous prior to the separate strain maintenance.

The production of hybrid maize lines typically comprises planting in pollinating proximity seeds of, for example, inbred maize line NP2073 and of a different inbred parent maize plant, cultivating the seeds of inbred maize line NP2073 and of said different inbred parent maize plant into plants that bear flowers, emasculating the male flowers of inbred maize line NP2073 or the male flowers of said different inbred parent maize plant to produce an emasculated maize plant, allowing cross-pollination to occur between inbred maize line NP2073 and said different inbred parent maize plant and harvesting seeds produced on said emasculated maize plant. The harvested seed are grown to produce hybrid maize plants.

Inbred maize line NP2073 can be crossed to inbred maize lines of various heterotic group (see e.g. Hallauer et al. (1988) in Corn and Corn Improvement, Sprague et al, eds, chapter 8, pages 463–564) for the production of hybrid maize lines.

TABLE I

VARIETY DESCRIPTION INFORMATION
Inbred maize line NP2073 is compared to inbred A632

| | INBRED NP2073 | | | INBRED A632 | | |
|---|---|---|---|---|---|---|
| MATURITY | Days | Heat Units | | Days | Heat Units | |
| From emergence to 50% of plants in silk | 64 | 1353.0 | | 68 | 1441.3 | |
| From emergence to 50% of plants in pollen | 63 | 1338.0 | | 66 | 1400.2 | |
| From 10% to 90% pollen shed | 003 | 0097.1 | | 003 | 0073.3 | |

| PLANT | | Std Dev | Sample Size | | Std Dev | Sample Size |
|---|---|---|---|---|---|---|
| cm Plant Height (to tassel tip) | 196.2 | 30.43 | 6 | 200.7 | 37.14 | 6 |
| cm Ear Height (to base of top ear node) | 66.8 | 15.78 | 6 | 76.2 | 16.04 | 6 |
| cm Length of Top Ear Internodenode | 009.5 | 4.03 | 6 | 10.1 | 4.42 | 6 |
| Average Number of Tillers | 0 | 0 | 4 | 0 | 0.0 | 4 |
| Average Number of Ears per Stalk | 1.1 | 0.12 | 6 | 1.6 | 0.53 | 6 |
| Anthocyanin of Brace Roots: 1 = Absent 2 = Faint 3 = Moderate 4 = Dark | 3 | | | 4 | | |

| LEAF | | Std Dev | Sample Size | | Std Dev | Sample Size |
|---|---|---|---|---|---|---|
| cm Width of Ear Node Leaf | 007.5 | 3.00 | 6 | 007.0 | 3.01 | 6 |
| cm Length of Ear Node Leaf | 054.3 | 35.43 | 4 | 054.3 | 35.21 | 4 |
| Number of leaves above top ear | 5 | 0.40 | 6 | 6 | 0.26 | 6 |
| Degrees Leaf Angle (measure from 2$^{nd}$ leaf above ear at Anthesis to stalk above leaf) | 47 | 19.40 | 6 | 061 | 26.02 | 6 |
| Leaf Color (Munsell code 5GY 4/4) | 02 | | | 02 | | |
| Leaf Sheath Pubescence (Rate on scale from 1 = none to 9 = like peach fuzz) | 3 | | | 6 | | |
| Marginal Waves (Rate on scale from 1 = none to 9 = many) | 5 | | | 5 | | |
| Longitudinal Creases (Rate on scale from 1 = none to 9 = many) | 6 | | | 6 | | |
| TASSEL | | | | | | |
| Number of Primary Lateral Branches | 6 | 0.42 | 6 | 7 | 1.10 | 6 |
| Branch Angle from Central Spike | 79 | 3.21 | 6 | 59 | 16.37 | 6 |
| Cm Tassel Length (from top leaf collar to tassel tip) | 30.4 | 13.92 | 6 | 25.7 | 10.92 | 6 |
| Pollen Shed (Rate on scale from 0 = male sterile to 9 = heavy shed) | 7 | | | 6 | | |
| Anther Color | 05 | (Munsell code 2.5GY 8/6) | | 26 | (Munsell code) | |
| Glume Color | 26 | (Munsell code) | | 26 | (Munsell code) | |
| Bar Glumes (Glume Bands): 1=Absent 2 = Present | 2 | | | 2 | | |

TABLE I-continued

VARIETY DESCRIPTION INFORMATION
Inbred maize line NP2073 is compared to inbred A632

| | INBRED NP2073 | | | INBRED A632 | | |
|---|---|---|---|---|---|---|
| EAR (Unhusked Data) | | | | | | |
| Silk Color (3 days after emergence) | 17 | (Munsell code 5RP 3/8) | | 05 | (Munsell code 2.5GY 8/8) | |
| Fresh Husk Color (25 days after 50% silking) | 02 | (Munsell code 2.5GY 7/6) | | 02 | (Munsell code 5GY 6/8) | |
| Dry Husk Color (65 days after 50 % silking) | 22 | (Munsell code 2.5Y 8/4) | | 22 | (Munsell code 2.5Y 8/4) | |
| Position of Ear at Dry Husk Stage: 1 = Upright 2 = Horizontal 3 = Pendent | 1 | | | 1 | | |
| Husk Tightness (Rate on scale from 1 = very loose to 9 = very tight) | 5 | | | 5 | | |
| Husk Extension (at harvest): 1 = Short (ears exposed) 2 = Medium (<8cm) 3 = Long (8-10 cm beyond ear tip) 4 = Very long (>10 cm) | 2 | | | 4 | | |

| EAR (Husked Ear Data) | | Std Dev | Sample Size | | Std Dev | Sample Size |
|---|---|---|---|---|---|---|
| Cm Ear Length | 15.4 | 0.42 | 6 | 14.9 | 0.43 | 5 |
| mm Ear Diameter at mid-point | 39.5 | 2.01 | 6 | 36.4 | 1.61 | 4 |
| gm Ear Weight | 99.0 | 14.73 | 6 | 64.8 | 17.98 | 4 |
| Number of Kernel Rows | 14 | 0.70 | 6 | 15 | 0.07 | 4 |
| Kernel Rows: 1 = Indistinct 2 = Distinct | 2 | | | 2 | | |
| Row Alignment: 1 = Straight 2 = Slightly Curved 3 = Spiral | 2 | | | 2 | | |
| cm Shank Length | 7.2 | 1.01 | 6 | 8.5 | 3.50 | 5 |
| Ear Taper: 1 = Slight 2 = Average 3 = Extreme | 2 | | | 2 | | |

| KERNEL (Dried) | | Std Dev | Sample Size | | Std Dev | Sample Size |
|---|---|---|---|---|---|---|
| mm Kernel Length | 10.7 | 0.29 | 6 | 9.3 | 1.06 | 4 |
| mm Kernel Width | 7.7 | 0.29 | 6 | 7.0 | 0.0 | 4 |
| mm Kernel Thickness | 3.7 | 0.76 | 6 | 4.8 | 0.35 | 4 |
| % Round Kernels (Shape Grade) | 22.2 | 16.99 | 6 | 63.3 | 18.03 | 4 |
| Aleurone Color Pattern: 1 = Homozygous 2 = Segregating | 1 | | | 1 | | |
| Aleurone Color | 19 | (Munsell code) | | 26 | (Munsell code) | |
| Hard Endosperm Color | 07 | (Munsell code 2.5Y 8/10) | | 07 | (Munsell code 2.5Y 8/0) | |
| Endosperm Type: 1 = Sweet (sul) 2 = Extra Sweet (sh2) 3 = Normal Starch | 3 | | | 3 | | |
| Gm Weight per 100 Kernels (unsized sample) | 26.3 | | | 23.9 | | |

| COB | | Std Dev | Sample Size | | Std Dev | Sample Size |
|---|---|---|---|---|---|---|
| mm Cob Diameter at mid-point | 21.9 | 0.36 | 6 | 22.9 | 0.85 | 4 |
| Cob Color | 13 | (Munsell code 5R 3/10) | | 13 | (Munsell code 5R 4/8) | |
| DISEASE RESISTANCE (1 = most susceptible to 9 = most resistant) | | | | | | |
| Eye Spot (Kabatiella zeae) | 8 | | | 6 | | |
| Northern Leaf Blight | 8 | Mixed Inoc. | | 7 | Mixed Inoc. | |
| Gray Leaf Spot | | | | | | |
| Common Rust | 4 | | | 6 | | |
| INSECT RESISTANCE(Rate from 1 = most susceptible to 9 = most resistant) | | | | | | |
| European Corn Borer(Osstrinia nubilalis) 1st Generation (Typically Whorl Leaf Feeding) | 2 | | | 6 | | |
| 2nd Generation Corn Borer | | | | | | |
| AGRONOMIC TRAITS | | | | | | |
| Stay Green (at 65 days after anthesis) (rate on scale from 1 = worst to 9 = excellent) | | | | | | |
| % Dropped Ears (at 65 days after anthesis) | 0 | | | 0 | | |
| % Pre-anthesis Brittle snapping | 2 | | | 1 | | |
| % Pre-anthesis Root Lodging | 6 | | | 5 | | |

TABLE I-continued

VARIETY DESCRIPTION INFORMATION
Inbred maize line NP2073 is compared to inbred A632

|  | INBRED NP2073 | INBRED A632 |
|---|---|---|
| % Post-anthesis Root Lodging (at 65 days after anthesis) | 0 | 0 |
| Kg/ha Yield of Inbred Per Se (at 12–13% grain moisture) | 3775 | 1624 |

In interpreting the foregoing color designations, reference may be made to the Munsell Glossy Book of Color, a standard color reference. Color codes: 1. light green, 2. medium green, 3. dark green, 4. very dark green, 5. green-yellow, 6. pale yellow, 7. yellow, 8. yellow-orange, 9. salmon, 10. pink-orange, 11. pink 12. light red, 13. cherry red, 14. red, 15. red and white, 16. pale purple, 17. purple, 18. colorless, 19. white, 20, white capped, 21. buff, 22. tan, 23. brown, 24. bronze, 25. variegated, 26. other.

Other comments to help interpret the data contained in Table I are as follows:

1) Heat Units per day were calculated using the standard formula: HU={MaxTemp (86)+Min Temp (50)]/2–50.
2) Large standard deviations are probably due to environmental factors at each individual location where the variety was observed. Since the varieties reported in this exhibit are inbreds, the response to the environment is probably more pronounced than a hybrid or a combination of these inbred lines. Any stress at specific times during the growing season could influence results.
3) Glume color of NP2073 is 05 or green-yellow (2.5GY 7/6) and/or 05 or green-yellow with 16 or pale purple shaded areas. There also seems to be 16 or pale purple coloring on the margin of the glume.
4) The NP2073 glume has purple tips.
5) The glume color bars of NP2073 appear light 05 or light green-yellow to almost 19 or white.
6) The anther color of A632 appears 06 or pale yellow (2.5Y 8/6) with a faint 16 or pale purple shade.
7) The glume color of A632 is 02 or medium-green (5GY 7/6) with purple shade.
8) The glume of A632 has purple tips.
9) The glume color bars of A632 have a 16 or pale purple shade.
10) The aluerone color for A632 is 19 or white with a reddish shade.
11) The Disease and Insect data for both NP2073 and A632 were taken in 2000 at Stanton, Minn. (2 reps.).

The corn inbred line NP2073 is most similar to the PVP Standard Inbred Line A632. Comparisons of the two varieties were conducted in "side-by-side" trials in 1999 and 2000 at two different sites. The trial locations were Stanton, Minn. and Janesville, Wis. The trials had two replications at each site. Plot size was 152 cm×518 cm. Each plot had approximately 50 plants.

NP2073 differs from A632 for several different traits. The silk emergence for the variety NP2073 is earlier at 1353.0 heat units as compared to A632 at 1441.3 heat units. The days from emergence to 50% silk is less for NP2073 than A632 at 64 days as compared to 68.

The plant appearance of NP2073 differs significantly from A632. The ear height of NP2073 is shorter at 66.8 cm than A632 at 76.2 cm. The anthocyanic pigmentation of the brace roots is rated a "3" or "moderate" for NP2171 and "4" or "dark" for A632. The average number of ears per stalk on NP2073 is 1 and it is 2 for A632.

Some of the more pronounced differences between NP2073 and A632 occur in the tassel. The NP2073 tassel branches are very "upright" in appearance in contrast to A632. The NP2073 tassel has fewer primary branches with 6 as compared to 7 on A619.

The pollen shed rating for NP2073 is a 7 and A632 is a 6 (see Exhibit D Table 4—1999 and 2000 Data—NP2073 vs. A632 Comparisons). The anther color of NP2171 is 05 or green-yellow (Munsell Color—2.5GY 8/6) and A632 is 06 or pale yellow (Munsell Color—2.5GY 8/6) with a faint 16 or pale purple shade. The glume color of NP2073 is 05 or green-yellow (Munsell Color—2.5GY 7/6) and 05 or green-yellow with 16 or pale purple shaded areas. There also seems to be a 16 or pale purple coloring on the margins of the NP2073 glume. The glume color of A632 is 02 or medium green (Munsell Color—5GY 7/6) with purple shade. The glume color bars of NP2073 appear light 05 or light green-yellow to almost 19 or white. The A619 glume color bars are 16 or pale purple. There are some purple "tips" to both the NP2073 and A632 glume.

The silk color of NP2073 is 17 or purple (Munsell Color—5RP 3/8). The A632 silk is 05 or green-yellow (Munsell Color—2.5GY 8/8).

The husk extension of NP2073 is rated a "2" as compared to A632, which is rated a "4" (see Exhibit D Table 4—1999 and 2000 Data—NP2073 vs. A632 Comparisons).

The NP2073 kernel row number is 14 and A632 is 15 (see Exhibit D Table 4— 1999 and 2000 Data—NP2073 vs. A632 Comparisons).

NP2073 has a smaller cob diameter at the mid-point than A632. The NP2073 cob is 21.9 mm while the A632 cob is 22.9 mm (see Exhibit D Table 4—1999 and 2000 Data—NP2073 vs. A632 Comparisons).

The kernels of the two inbreds differ greatly. NP2073 has a longer kernel than A632. NP2073 is 10.7 mm long as compared to 9.3 mm on A632 (see Exhibit D Table 4—1999 and 2000 Data—NP2073 vs. A632 Comparisons). The aleurone color of the NP2073 is 19 or white while the A632 kernel appears to be 19 or white with a slight reddish shade.

The disease and insect resistance of the two inbreds also has some significant differences (see Exhibit C). The Eyespot rating for NP2073 is "8" and a "6" for A632. The First Brood European Corn Borer rating of NP2073 is a "2" and A619 a "6".

NP2073 is a higher yielding inbred than A632. The Kg/Ha yield of NP2073 is 3775 and is 1624 for A632.

Origin and Breeding History of Corn Inbred Line NP2073

Inbred line NP2073 was derived from the initial cross of inbred Y9017 and inbred line H8431, which was then backcrossed to H8431. Inbred line H8431 is an inbred line developed by Syngenta Seeds. Inbred line Y9017 is an inbred line also developed by Syngenta Seeds. After development of the $BC_1$ population of Y9017/H8431*1, the breeding method was simple pedigree ear-to row for the development of inbred line NP2073.

The details of the development stage for inbred line NP2073 are as follows:

1990/91 Puerto Rico: H8431 was crossed to Y9017 to produce $F_1$ seed

1991 Janesville, Wis.: H8431 was backcrossed to generate Y9017/H8431*1 BC1 ($S_0$) seed 1991/92 Kauai, Hi.: Plants of the $S_0$ were self-pollinated to produce the $S_1$.

1992 Janesville, Wis.: Ear rows of the $S_1$ families were grown, and plants were self-pollinated to produce the $S_2$ generation. Testcrosses of the $S_1$ families were made. Phenotypic selection of the $S_1$ families was practiced for resistance to diseases, synchrony of pollen shed and silk, and kernel quality.

1992/93 Kauai, Hi.: Plants of the $S_2$ families were self-pollinated to produce the $S_3$ generation.

1993 Janesville, Wis.: Ear rows of the $S_3$ families were grown and self-pollinated to produce the $S_4$ generation. Testcrosses of the $S_3$ families were made. Testcrosses were grown at several locations. Selection of $S_3$ families was based upon the testcrosses for grain yield, grain moisture at harvest, and resistance to stalk and root lodging. Phenotypic selection of the $S_3$ families was continued for resistance to diseases, synchrony of pollen shed and silk, and kernel quality.

1993/94 Kauai, Hi.: Plants of the $S_4$ families were self-pollinated to produce the $S_5$ generation. Testcrosses of the $S_4$ family were made.

1994 Janesville, Wis.: Ear rows of the $S_5$ families were grown and self-pollinated to produce the $S_6$ generation. Testcrosses of the $S_5$ families were made. $S_4$ Testcrosses were grown at several locations. Selection of $S_5$ families was based upon the testcrosses for grain yield, grain moisture at harvest, and resistance to stalk and root lodging. Phenotypic selection of the $S_5$ families was continued for resistance to diseases, synchrony of pollen shed and silk, and kernel quality.

1994/95 Kauai, Hi.: Plants of the $S_6$ families were self pollinated to produce the $S_7$ generation. Testcrosses of the $S_6$ families were made.

1995 Janesville, Wis.: Ear rows of each of the $S_7$ families were grown, and plants were self-pollinated to produce the $S_8$ generation. Testcrosses of the $S_7$ families were made. Testcrosses were grown at several locations. Selection of $S_7$ families was based upon the testcrosses for grain yield, grain moisture at harvest, and resistance to stalk and root lodging. Plants within the $S_7$ family were closely evaluated for uniformity of anther and silk color, plant and ear height, and other characteristics.

1995/96 Kauai, Hi.: Rows of each $S_8$ ear culture were grown and self-pollinated to produce "breeder's seed". Plants were closely evaluated for uniformity of anther and silk color, plant and ear height, and other characteristics. Isozyme test (12 compounds) confirmed the purity of the inbred line NP2073.

From 1995 to 1997 the inbred line has been observed in Janesville, Wis., Hampton, Iowa, Stanton, Minn. and other locations. No phenotypic or isozymic variants have been observed from 1995 to present. The inbred NP2073 has been uniform and stable from 1995 to 1997 during at least five generations of propagation.

The invention also encompasses plants of inbred maize line NP2073 and parts thereof further comprising one or more specific, single gene traits which have been introgressed into inbred maize line NP2073 from another maize line. Preferably, one or more new traits are transferred to inbred maize line NP2073, or, alternatively, one or more traits of inbred maize line NP2073 are altered or substituted. The transfer (or introgression) of the trait(s) into inbred maize line NP2073 is for example achieved by recurrent selection breeding, for example by backcrossing. In this case, inbred maize line NP2073 (the recurrent parent) is first crossed to a donor inbred (the non-recurrent parent) that carries the appropriate gene(s) for the trait(s) in question. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes (see, for example, Poehlman & Sleper (1995) Breeding Field Crops, 4th Ed., 172–175; Fehr (1987) Principles of Cultivar Development, Vol. 1: Theory and Technique, 360–376).

The laboratory-based techniques described above, in particular RFLP and SSR, are routinely used in such backcrosses to identify the progenies having the highest degree of genetic identity with the recurrent parent. This permits to accelerate the production of inbred maize lines having at least 90%, preferably at least 95%, more preferably at least 99% genetic identity with the recurrent parent, yet more preferably genetically identical to the recurrent parent, and further comprising the trait(s) introgressed from the donor patent. Such determination of genetic identity is based on molecular markers used in the laboratory-based techniques described above. Such molecular markers are for example those known in the art and described in Boppenmaier, et al., "Comparisons among strains of inbreds for RFLPs", Maize Genetics Cooperative Newsletter (1991) 65, pg. 90, or those available from the University of Missouri database and the Brookhaven laboratory database. The last backeross generation is then selfed to give pure breeding progeny for the gene(s) being transferred. The resulting plants have essentially all of the morphological and physiological characteristics of inbred maize line NP2073, in addition to the single gene trait(s) transferred to the inbred. Preferably, the resulting plants have all of the morphological and physiological characteristics of inbred maize line NP2073, in addition to the single gene trait(s) transferred to the inbred. The exact backerossing protocol will depend on the trait being altered to determine an appropriate testing protocol. Although backcrossing methods are simplified when the trait being transferred is a dominant allele, a recessive allele may also be transferred. In this instance it may be necessary to introduce a test of the progeny to determine if the desired trait has been successfully transferred.

Many traits have been identified that are not regularly selected for in the development of a new inbred but that can be improved by backcrossing techniques or genetic transformation. Examples of traits transferred to inbred maize line NP2073 include, but are not limited to, waxy starch, herbicide tolerance, resistance for bacterial, fungal, or viral disease, insect resistance, enhanced nutritional quality, improved performance in an industrial process, altered reproductive capability, such as male sterility or male fertility, yield stability and yield enhancement. Other traits transferred to inbred maize line NP2073 are for the production of commercially valuable enzymes or metabolites in plants of inbred maize line NP2073.

Traits transferred to maize inbred line NP2073 are naturally occurring maize traits, which are preferably introgressed into inbred maize line NP2073 by breeding methods such as backcrossing, or are heterologous transgenes, which are preferably first introduced into a maize line by genetic transformation using genetic engineering and transformation techniques well known in the art, and then introgressed into inbred line NP2073. Alternatively a heterologous trait is directly introduced into inbred maize line NP2073 by genetic transformation. Heterologous, as used herein, means of different natural origin or represents a non-natural state. For example, if a host cell is transformed with a nucleotide sequence derived from another organism, particularly from another species, that nucleotide sequence is heterologous with respect to that host cell and also with respect to descendants of the host cell which carry that gene. Similarly, heterologous refers to a nucleotide sequence derived from and inserted into the same natural, original cell type, but which is present in a non-natural state, e.g. a different copy number, or under the control of different regulatory sequences. A transforming nucleotide sequence may comprise a heterologous coding sequence, or heterologous regulatory sequences. Alternatively, the transforming nucleotide sequence may be completely heterologous or may comprise any possible combination of heterologous and endogenous nucleic acid sequences.

A transgene introgressed into maize inbred line NP2073 typically comprises a nucleotide sequence whose expression is responsible or contributes to the trait under the control of a promoter appropriate for the expression of the nucleotide sequence at the desired time in the desired tissue or part of the plant. Constitutive or inducible promoters are used. The transgene may also comprise other regulatory elements such as for example translation enhancers or termination signals. In a preferred embodiment, the nucleotide sequence is the coding sequence of a gene and is transcribed and translated into a protein. In another preferred embodiment, the nucleotide sequence encodes an antisense RNA, a sense RNA that is not translated or only partially translated, a t-RNA, a r-RNA or a sn-RNA.

Where more than one trait are introgressed into inbred maize line NP2073, it is preferred that the specific genes are all located at the same genomic locus in the donor, non-recurrent parent, preferably, in the case of transgenes, as part of a single DNA construct integrated into the donor's genome. Alternatively, if the genes are located at different genomic loci in the donor, non-recurrent parent, backcrossing allows to recover all of the morphological and physiological characteristics of inbred maize line NP2073 in addition to the multiple genes in the resulting maize inbred line.

The genes responsible for a specific, single gene trait are generally inherited through the nucleus. Known exceptions are, e.g. the genes for male sterility, some of which are inherited cytoplasmically, but still act as single gene traits. In a preferred embodiment, a heterologous transgene to be transferred to maize inbred line NP2073 is integrated into the nuclear genome of the donor, non-recurrent parent. In another preferred embodiment, a heterologous transgene to be transferred to into maize inbred line NP2073 is integrated into the plastid genome of the donor, non-recurrent parent. In a preferred embodiment, a plastid transgene comprises one gene transcribed from a single promoter or two or more genes transcribed from a single promoter.

In a preferred embodiment, a transgene whose expression results or contributes to a desired trait to be transferred to maize inbred line NP2073 comprises a virus resistance trait such as, for example, a MDMV strain B coat protein gene whose expression confers resistance to mixed infections of maize dwarf mosaic virus and maize chlorotic mottle virus in transgenic maize plants (Murry et al. Biotechnology (1993) 11:1559–64). In another preferred embodiment, a transgene comprises a gene encoding an insecticidal protein, such as, for example, a crystal protein of *Bacillus thuringiensis* or a vegetative insecticidal protein from *Bacillus cereus*, such as VIP3 (see for example Estruch et al. Nat Biotechnol (1997) 15:137–41). In a preferred embodiment, an insecticidal gene introduced into maize inbred line NP2073 is a Cry1Ab gene or a portion thereof, for example introgressed into maize inbred line NP2073 from a maize line comprising a Bt-11 event as described in U.S. Pat. No. 6,114,608, which is incorporated herein by reference, or from a maize line comprising a 176 event as described in Koziel et al. (1993) Biotechnology 11: 194–200. In yet another preferred embodiment, a transgene introgressed into maize inbred line NP2073 comprises a herbicide tolerance gene. For example, expression of an altered acetohydroxyacid synthase (AHAS) enzyme confers upon plants tolerance to various imidazolinone or sulfonamide herbicides (U.S. Pat. No. 4,761,373). In another preferred embodiment, a non-transgenic trait conferring tolerance to imidazolinones is introgressed into maize inbred line NP2073 (e.g a "IT" or "IR" trait). U.S. Pat. No. 4,975,374 relates to plant cells and plants containing a gene encoding a mutant glutamine synthetase (GS) resistant to inhibition by herbicides that are known to inhibit GS, e.g. phosphinothricin and methionine sulfoximine. Also, expression of a Streptomyces bar gene encoding a phosphinothricin acetyl transferase in maize plants results in tolerance to the herbicide phosphinothricin or glufosinate (U.S. Pat. No. 5,489,520). U.S. Pat. No. 5,013,659 is directed to plants that express a mutant acetolactate synthase (ALS) that renders the plants resistant to inhibition by sulfonylurea herbicides. U.S. Pat. No. 5,162,602 discloses plants tolerant to inhibition by cyclohexanedione and aryloxyphenoxypropanoic acid herbicides. The tolerance is conferred by an altered acetyl coenzyme A carboxylase(ACCase). U.S. Pat. No. 5,554,798 discloses transgenic glyphosate tolerant maize plants, which tolerance is conferred by an altered 5-enolpyruvyl-3-phosphoshikimate (EPSP) synthase gene. U.S. Pat. No. 5,804,425 discloses transgenic glyphosate tolerant maize plants, which tolerance is conferred by an EPSP synthase gene derived from *Agrobacterium tumefaciens* CP-4 strain. Also, tolerance to a protoporphyrinogen oxidase inhibitor is achieved by expression of a tolerant protoporphyrinogen oxidase enzyme in plants (U.S. Pat. No. 5,767,373). Another trait transferred to inbred maize line NP2073 confers tolerance to an inhibitor of the enzyme hydroxyphenylpyruvate dioxygenase (HPPD) and transgenes conferring such trait are, for example, described in WO 9638567, WO 9802562, WO 9923886, WO 9925842, WO 9749816, WO 9804685 and WO 9904021. All issued patents referred to herein are, in their entirety, expressly incorporated herein by reference.

In a preferred embodiment, a transgene transferred to maize inbred line NP2073 comprises a gene conferring tolerance to a herbicide and at least another nucleotide sequence encoding another trait, such as for example, an insecticidal protein. Such combination of single gene traits is for example a Cry1Ab gene and a bar gene.

Specific transgenic events introgressed into maize inbred line NP2073 can be obtained through the list of Petitions of Nonregulated Status Granted by APHIS as of Oct. 12, 2000. For example, introgressed from glyphosate tolerant event GA21 (9709901p), glyphosate tolerant/Lepidopteran insect resistant event MON 802 (9631701p), Lepidopteran insect resistant event DBT418 (9629101p), male sterile event MS3 (9522801p), Lepidopteran insect resistant went Bt11 (9519501p), phosphinothricin tolerant event B16 (9514501p), Lepidopteran insect resistant event MON 80100 (9509301p), phosphinothricin tolerant events T14, T25 (9435701p), Lepidopteran insect resistant event 176 (9431901p).

The introgression of a Bt11 event into a maize line, such as maize inbred line NP2073, by backcrossing is exemplified in U.S. Pat. No. 6,114,608, and the present invention is directed to methods of introgressing a Bt11 event into maize inbred line NP2073 using for example the markers described in U.S. Pat. No. 6,114,608 and to resulting maize lines.

Direct selection may be applied where the trait acts as a dominant trait. An example of a dominant trait is herbicide tolerance. For this selection process, the progeny of the initial cross are sprayed with the herbicide prior to the backcrossing. The spraying eliminates any plant which do not have the desired herbicide tolerance characteristic, and only those plants that have the herbicide tolerance gene are used in the subsequent backcross. This process is then repeated for the additional backcross generations.

This invention also is directed to methods for producing a maize plant by crossing a first parent maize plant with a second parent maize plant wherein either the first or second parent maize plant is a maize plant of inbred line NP2073 or a maize plant of inbred line NP2073 further comprising one or more single gene traits. Further, both first and second parent maize plants can come from the inbred maize line NP2073 or an inbred maize plant of NP2073 further comprising one or more single gene traits. Thus, any such methods using the inbred maize line NP2073 or an inbred maize plant of NP2073 further comprising one or more single gene traits are part of this invention: selfing, backcrosses, hybrid production, crosses to populations, and the like. All plants produced using inbred maize line NP2073 or inbred maize plants of NP2073 further comprising one or more single gene traits as a parent are within the scope of this invention. Advantageously, inbred maize line NP2073 or inbred maize plants of NP2073 further comprising one or more single gene traits are used in crosses with other, different, maize inbreds to produce first generation (F1) maize hybrid seeds and plants with superior characteristics.

In a preferred embodiment, seeds of inbred maize line NP2073 or seeds of inbred maize plants of NP2073 further comprising one or more single gene traits are provided as an essentially homogeneous population of inbred corn seeds. Essentially homogeneous populations of inbred seed are those that consist essentially of the particular inbred seed, and are generally purified free from substantial numbers of other seed, so that the inbred seed forms between about 90% and about 100% of the total seed, and preferably, between about 95% and about 100% of the total seed. Most preferably, an essentially homogeneous population of inbred corn seed will contain between about 98.5%, 99%, 99.5% and about 100% of inbred seed, as measured by seed grow outs. The population of inbred corn seeds of the invention is further particularly defined as being essentially free from hybrid seed. The inbred seed population may be separately grown to provide an essentially homogeneous population of plants of inbred maize line NP2073 or inbred maize plants of NP2073 further comprising one or more single gene traits.

As used herein, the term "plant" includes plant cells, plant protoplasts, plant cell tissue cultures from which maize plants can be regenerated, plant calli, plant clumps, and plant cells that are intact in plants or parts of plants, such as embryos, pollen, ovules, flowers, kernels, ears, cobs, leaves, husks, stalks, roots, root tips, anthers, silk, seeds and the like.

Duncan, Williams, Zehr, and Widholm, Planta (1985) 165:322–332 reflects that 97% of the plants cultured that produced callus were capable of plant regeneration. Subsequent experiments with both inbreds and hybrids produced 91% regenerable callus that produced plants. In a further study in 1988, Songstad, Duncan & Widholm in Plant Cell Reports (1988), 7:262–265 reports several media additions that enhance regenerability of callus of two inbred lines. Other published reports also indicated that "nontraditional" tissues are capable of producing somatic embryogenesis and plant regeneration. K. P. Rao, et al., Maize Genetics Cooperation Newsletter, 60:64–65 (1986), refers to somatic embryogenesis from glume callus cultures and B. V. Conger, et al., Plant Cell Reports, 6:345–347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture procedures of maize are described in Green and Rhodes, "Plant Regeneration in Tissue Culture of Maize," Maize for Biological Research (Plant Molecular Biology Association, Charlottesville, Va. 1982, at 367–372) and in Duncan, et al., "The Production of Callus Capable of Plant Regeneration from Immature Embryos of Numerous Zea mays Genotypes," 165 Planta 322–332 (1985). Thus, another aspect of this invention is to provide cells that upon growth and differentiation produce maize plants having the physiological and morphological characteristics of inbred maize line NP2073. In a preferred embodiment, cells of inbred maize line NP2073 are transformed genetically, for example with one or more genes described above, for example by using a transformation method described in U.S. Pat. No. 6,114,608, and transgenic plants of inbred maize line NP2073 are obtained and used for the production of hybrid maize plants.

Maize is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry. Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications. Plant parts other than the grain of maize are also used in industry: for example, stalks and husks are made into paper and wallboard and cobs are used for fuel and to make charcoal.

The seed of inbred maize line NP2073 or of inbred maize line NP2073 further comprising one or more single gene traits, the plant produced from the inbred seed, the hybrid maize plant produced from the crossing of the inbred, hybrid seed, and various parts of the hybrid maize plant can be utilized for human food, livestock feed, and as a raw material in industry.

The present invention therefore also discloses an agricultural product comprising a plant of the present invention or derived from a plant of the present invention. The present invention also discloses an industrial product comprising a plant of the present invention or derived from a plant of the present invention. The present invention further discloses methods of producing an agricultural or industrial product comprising planting seeds of the present invention, growing plant from such seeds, harvesting the plants and processing them to obtain an agricultural or industrial product.

DEPOSIT

Applicants have made a deposit of at least 2500 seeds of Inbred Maize Line NP2073 with the American Type Culture Collection (ATCC), Manassas, Va., 20110-2209 U.S.A., ATCC Deposit No: PTA-2971. This deposit of the Inbred Maize Line NP2073 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801–1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. Seed of maize inbred line designated NP2073 representative seed of said maize inbred line having been deposited under ATCC Accession No. PTA-2971.

2. A maize plant, or a parts thereof, produced by growing the seed of claim 1.

3. Pollen of the plant of claim 2.

4. An ovule of the plant of claim 2.

5. A maize plant, or parts thereof, having all the physiological and morphological characteristics of the plant according to claim 2.

6. Seed produced by selfing the plant according to claim 2 or 5.

7. A tissue culture of regenerable cells of the maize plant according to claim 2.

8. The tissue culture according to claim 7, wherein the regenerable cells are from a tissue selected from the group consisting of embryos, meristems, pollen, leaves, anthers, roots, root tips, silk, flowers, kernels, ears, cobs, husks and stalks, or are protoplasts or callus produced therefrom.

9. A maize plant regenerated from the tissue culture of claim 7, wherein the regenerated plant has all the morphological and physiological characteristics of a plant of inbred line NP2073, seed of said inbred line having been deposited under ATCC Accesion No. PTA-2971.

10. A method for producing maize seed comprising crossing a first parent maize plant with a second parent maize plant and harvesting the resultant first generation maize seed, wherein said first or second parent maize plant is the inbred maize plant of claim 2.

11. The method according to claim 10, wherein said resultant seed is a first generation (F1) hybrid maize seed.

12. The method according to claim 10, wherein the inbred maize plant of claim 2 is the female parent.

13. The method according to claim 10, wherein the inbred maize plant of claim 2 is the male parent.

14. A method for producing maize seed comprising crossing a first parent maize plant with a second parent maize plant and harvesting the resultant first generation maize seed, wherein said first or second parent maize plant is the inbred maize plant of claim 5.

15. The method according to claim 14, wherein said resultant seed is a first generation (F1) hybrid maize seed.

16. The method according to claim 14, wherein the inbred maize plant of claim 5 is the female parent.

17. The method according to claim 14, wherein the inbred maize plant of claim 5 is the male parent.

* * * * *